(12) United States Patent
Naviero Sanchez et al.

(10) Patent No.: US 11,518,970 B2
(45) Date of Patent: Dec. 6, 2022

(54) SYSTEM FOR OBTAINING BIOMASS

(76) Inventors: Juan Carlos Naviero Sanchez, Santiago (CL); Christian Nelson Cruzat Hernandez, Vina del Mar (CL); Andrea Pilar Irarrazaval Olavarria, Vina del Mar (CL)

( * ) Notice: Subject to any disclaimer, the term of this patent is extended or adjusted under 35 U.S.C. 154(b) by 0 days.

(21) Appl. No.: 14/129,088

(22) PCT Filed: Jun. 24, 2011

(86) PCT No.: PCT/IB2011/052798
§ 371 (c)(1),
(2), (4) Date: Dec. 23, 2013

(87) PCT Pub. No.: WO2012/176021
PCT Pub. Date: Dec. 27, 2012

(65) Prior Publication Data
US 2014/0127766 A1 May 8, 2014

(51) Int. Cl.
*C12M 1/00* (2006.01)
*C12M 1/12* (2006.01)
*C12M 3/00* (2006.01)
*C12P 7/64* (2022.01)

(52) U.S. Cl.
CPC ............ *C12M 21/02* (2013.01); *C12M 23/04* (2013.01); *C12M 23/22* (2013.01); *C12M 23/48* (2013.01); *C12M 23/58* (2013.01); *C12M 27/18* (2013.01); *C12M 29/00* (2013.01); *C12M 29/08* (2013.01); *C12M 29/14* (2013.01); *C12P 7/64* (2013.01)

(58) Field of Classification Search
None
See application file for complete search history.

(56) References Cited

U.S. PATENT DOCUMENTS

| | | | |
|---|---|---|---|
| 4,868,123 A | 9/1989 | Berson et al. | |
| 2005/0255584 A1* | 11/2005 | Broneske | C12M 21/02 435/293.1 |
| 2007/0289206 A1* | 12/2007 | Kertz | A01G 15/00 47/1.4 |
| 2010/0034050 A1* | 2/2010 | Erb | B01F 3/04248 366/342 |
| 2011/0027875 A1* | 2/2011 | Cathcart | C12M 21/02 435/292.1 |

FOREIGN PATENT DOCUMENTS

| | | |
|---|---|---|
| DE | 3120105 A1 | 2/1983 |
| ES | 2347515 A1 | 10/2010 |
| WO | 2007098150 A2 | 8/2007 |
| WO | 2009077087 A1 | 6/2009 |
| WO | 2010068288 A2 | 6/2010 |
| WO | 2010138571 A1 | 12/2010 |

OTHER PUBLICATIONS

Youssef. 2010. Fluid dynamics and scale-up of bubble cols. with internals. Washington University in St. Louis. Dissertation towards partial fulfillment of the Ph.D. degree. Retrieved on Feb. 24, 2021. Downloaded from the internet: <https://core.ac.uk/download/pdf/233206429.pdf> pp. 1-160. specif. pp. 6,7.*
Miron, A.S. et al. 2000. Bubble-col. and airlift photobioreactors for algal culture. AlChE Journal 46(9): 1872-1887. specif. p. 1872.*
European Patent Application No. 11868266.5, Extended European Search Report dated Mar. 3, 2015.

* cited by examiner

*Primary Examiner* — Olivia M. Wise
*Assistant Examiner* — Sharon M. Papciak
(74) *Attorney, Agent, or Firm* — Eugenio J. Torres-Oyola; Victor M. Rodriguez-Reyes; Ferraiuoli LLC (57) ABSTRACT

This invention is a system for the production of biomass from photosynthesizing microorganisms that includes a photobioreactor comprising a transparent panel made from two transparent sheets with a separation between them, with top and bottom openings and with transparent, parallel subdivisions that form a panel of vertically arranged, transparent cells, where each transparent cell has a top opening and a bottom opening; a lower recirculation chamber in fluid contact with the bottom openings of the transparent panel; an upper recirculation chamber in fluid contact with the top openings of the transparent panel; a gas distribution tube externally arranged along the edge of said transparent panel; where said gas distribution tube comprises gas injectors arranged in fluid contact with the interior of a plurality of transparent cells; and a supporting structure that supports the transparent panel, the lower recirculation chamber, the upper recirculation chamber and the air distribution tube.

6 Claims, 6 Drawing Sheets

SYSTEM FOR OBTAINING BIOMASS

RELATED APPLICATIONS

This application is the National Phase of and claims the benefit of priority to International Application No. PCT/IB2011/052798, filed Jun. 24, 2011, which designated the U.S. and that International Application was published under PCT Article 21(2) in Spanish, which application is incorporated herein by reference in its entirety.

FIELD OF APPLICATION

This invention is related to the biotechnologies industry, and especially to a system that includes a photobioreactor for the production of biomass from photosynthesizing microorganisms.

BACKGROUND

The study and cultivation of microorganisms establishes optimal conditions for the successful production of biomass: for example, pH, viscosity, temperature, type of turbulence or agitation required to optimize residence times, and the mixing of a microorganism in a culture recirculating reactor. Depending on the biomass concentration and radiation intensity, it is usually said that light should penetrate to 10% of the thickness of a reactor to achieve optimal concentration of biomass.

Currently, several different types of photobioreactors using various light sources are used in biomass production. The state of the art includes a photobioreactor described in the international PCT application published as WO2005/006838, titled "Flat Panel Photobioreactor." This document describes an algae cultivation photobioreactor that comprises a disposable culture element, a cage-shaped structural component which supports the disposable element, and an aeration system. The disposable element is translucent or transparent and mainly comprises a plastic bag; the structural component is a wire grid which supports the disposable element, forming a flat panel, and the aeration system comprises an aeration tube in the bottom of said plastic bag. It also mentions that said structural component must be stable enough to withstand the pressure from the liquid culture medium, the aeration and heat exchanger accessories, and it must allow enough light to enter said culture medium for the photo-cultivation of algae. Said heat exchanger comprises pressurized tubing in contact with the culture medium through which a heating or cooling liquid circulates. We note that the solution proposed in this document involves a complex assembly of a grid that supports a flexible element and forces it into a flat, vertical position, it involves a recirculation system for the heat exchanger which requires additional energy consumption, and an aeration system by means of a distribution tube inside the plastic bag being held by said grid which does not allow the agitation generated produced in the culture medium to be optimized or controlled, making it possible for excess turbulence to be generated in some areas while others would have insufficient agitation, resulting in agglomeration and precipitation of the microorganisms in the plastic bag that contains the culture medium.

There is also a United States patent published as US2010/0323436 which describes a photobioreactor for large-scale micro-algae cultivation. Said photobioreactor includes multiple surface light source assemblies using light emitting diodes (LED), organic light-emitting diode (OLEO) elements, or an LED sheet as the light source. The surface light source assemblies former either a panel or cylinder and are installed at predetermined intervals in the space within the reaction tank, which is either cube or cylinder shaped, and emit light for the cultivation of photosynthesizing microorganisms. In addition, these surface light source assemblies are arranged in parallel and serve to divide the space inside the reaction tank and to increase the circulation of gas. The solution proposed in this document involves significant energy consumption in order to generate light by means of the illuminating surfaces included within the reactors. In fact, the solution described in said document is focused on solving a spatial limitation so that, by providing an internal light source in the form of inner partitions for the reactors, several reactors can be stacked on top of each other to increase the production of biomass per surface area. However, this solution to a spatial limitation entails high energy requirements and operational costs, and hence it would be very inefficient in an open system in an environment with unlimited space, when compared to a photobioreactor system that uses natural light.

Technical Problem

This invention addresses unresolved technical problems of art, such as energy efficiency for the large-scale economic feasibility of a system for obtaining biomass from photosensitizing microorganisms, by using a photobioreactor that meets the demands for optimal internal agitation, optimal light distribution and optimal biomass production per surface area used.

Technical Solution

In order to solve the technical problems indicated above, we present a system for obtaining biomass from photosynthesizing microorganisms based on a photobioreactor that comprises a transparent panel made from two transparent sheets with separation between them and greater than 90% transparency, with cell subdivisions that are exposed to natural light, along with gas injection into the plurality of cells to generate micro-vortices, thus achieving optimal light and agitation conditions for the growth of the culture, achieving high energy efficiency and economic feasibility.

This invention comprises a system for obtaining biomass from photosynthesizing microorganism; it includes a photobioreactor comprising a transparent panel made from two transparent sheets with separation between them, with greater than 90% transparency, with a top and bottom opening, with transparent, parallel subdivisions that form a panel of vertically arranged, transparent cells, where each transparent cell has a top and bottom opening; a lower recirculation chamber in fluid contact with the bottom opening of the transparent panel; an upper recirculation chamber in fluid contact with the top opening of the transparent panel; a gas distribution tube, arranged externally along the edge of said cell panel; where said gas distribution tube comprises gas injectors arranged in fluid contact with the interior of a plurality of transparent cells; and a supporting structure that supports the cell panel, the lower recirculation chamber, the upper recirculation chamber and the air distribution tube.

In addition, the air distribution tube and the collection chamber have intake and outflow connections to allow for a plurality of these photobioreactors, as per this invention, to be connected in parallel to form a system for obtaining biomass.

Technical Advantages

This invention allows better land utilization for biomass production and also increases energy efficiency sufficiently so as to permit biomass production.

DETAILED DESCRIPTION OF THE INVENTION

This invention comprises a system for producing biomass from photosynthesizing microorganisms that includes a batch-fed type photobioreactor that achieves greater energy efficiency. This invention achieves greater energy efficiency by using natural light, and the culture medium temperature is controlled through heat exchange with the environment.

Figure 1:
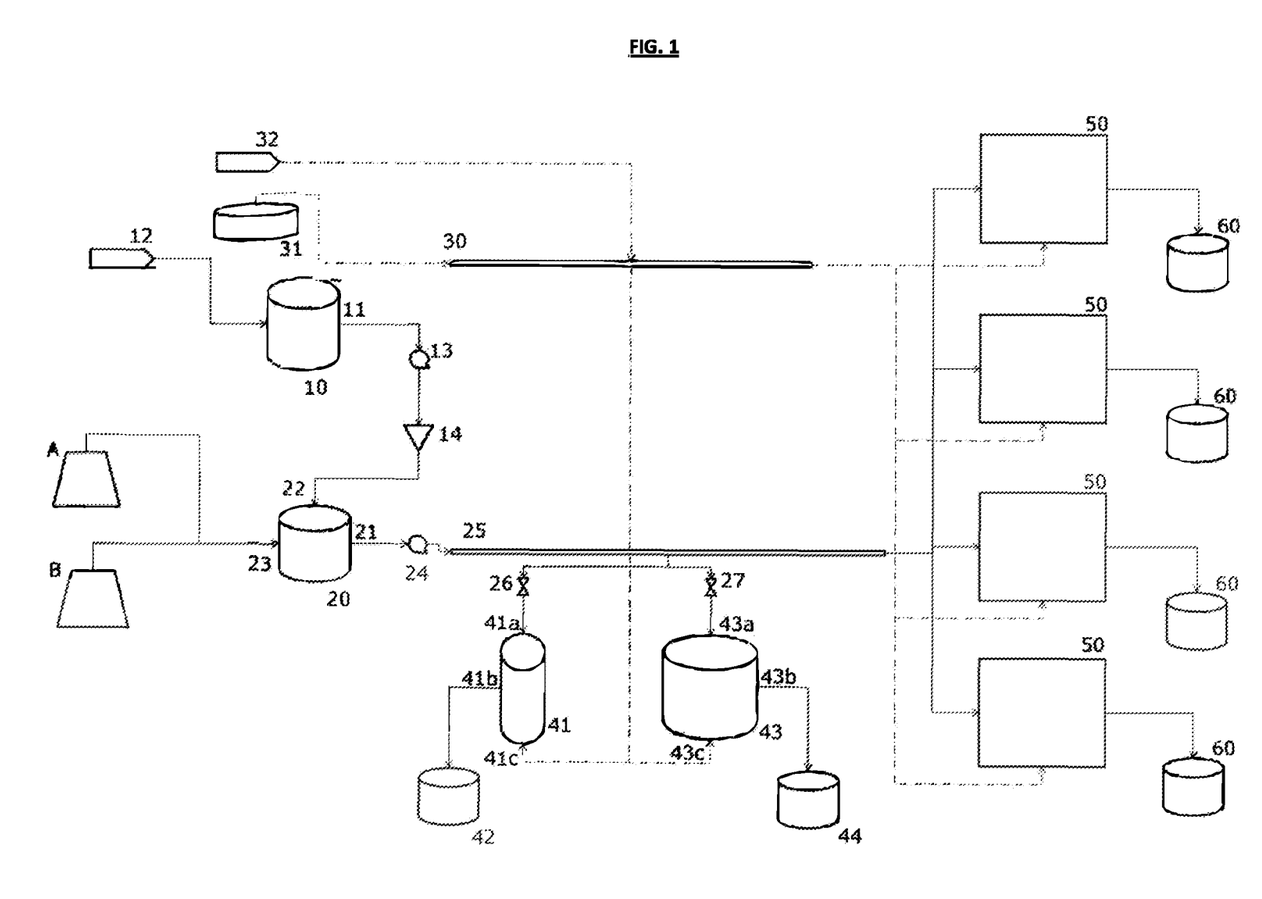
FIG. 1 is the system of this invention.
Figure 2:
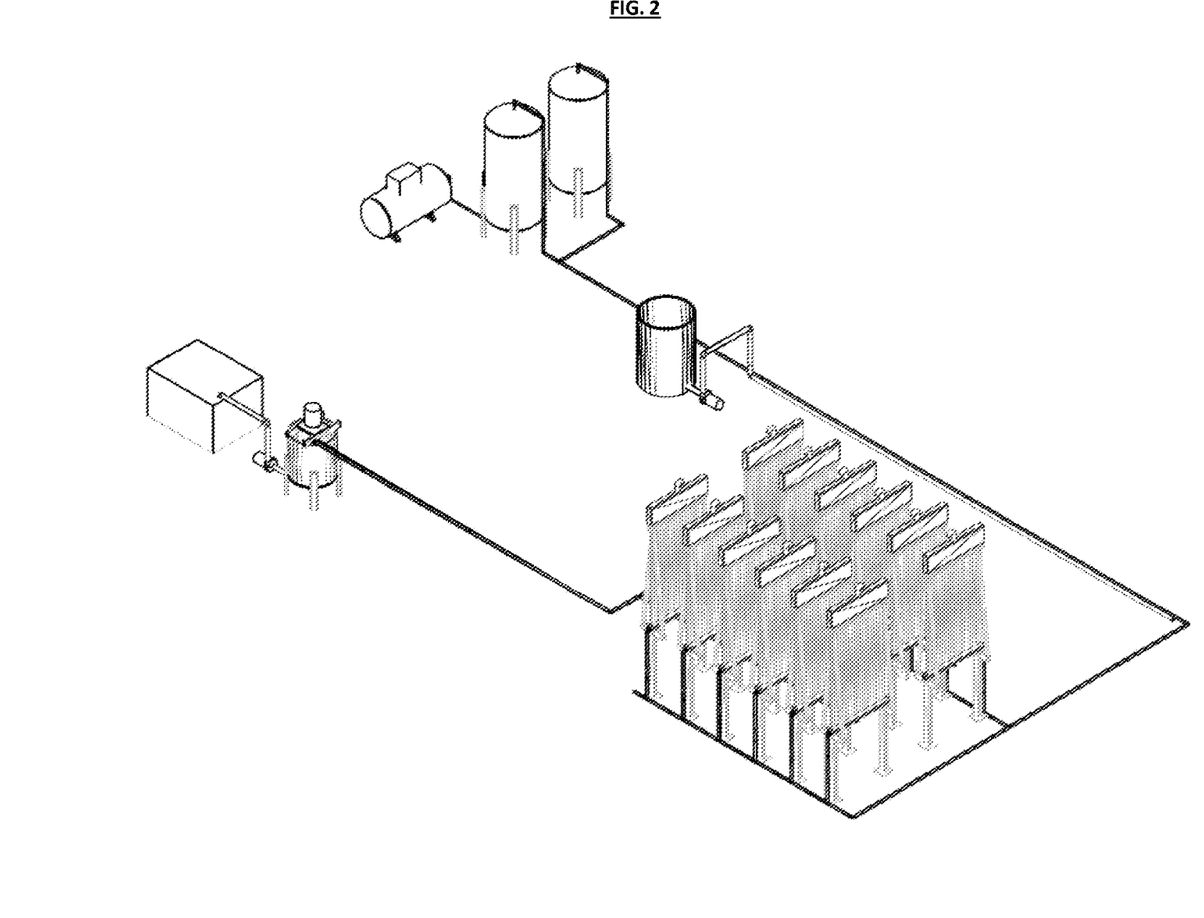
FIG. 2 is a schematic perspective view of the system of this invention.
Figure 3:
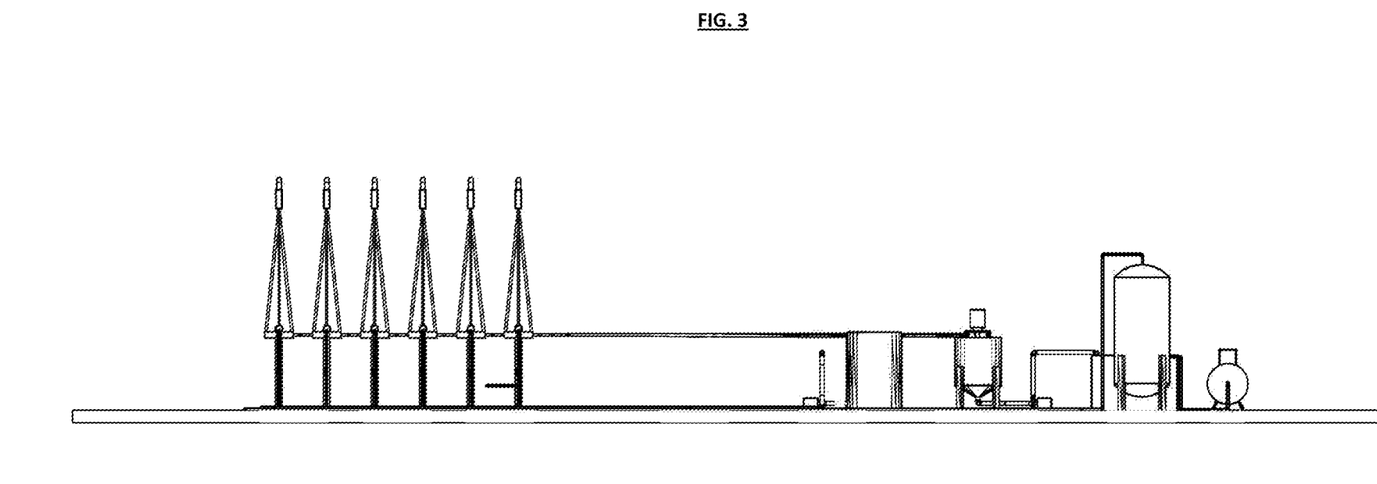
FIG. 3 is a schematic side elevation view of this invention.
Figure 4:
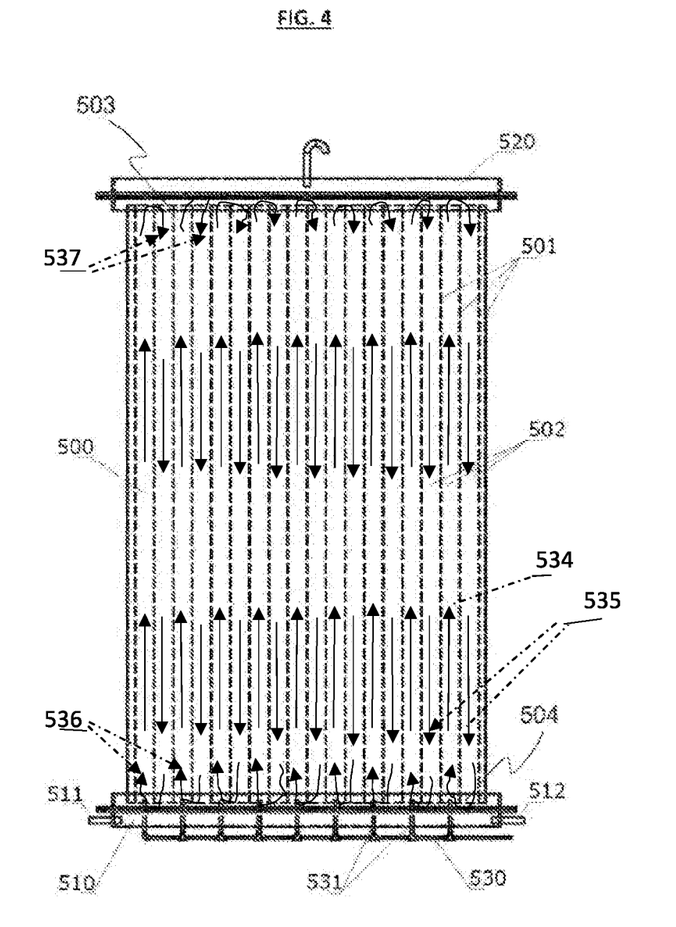
FIG. 4 is a schematic front elevation view of the transparent panel of the photobioreactor of this invention.
Figure 5:
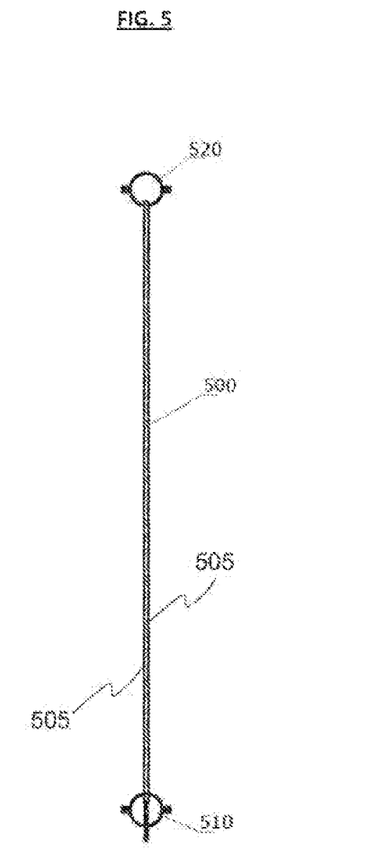
FIG. 5 is a side elevation view of a transparent panel for the photobioreactor of this invention.
Figure 6:
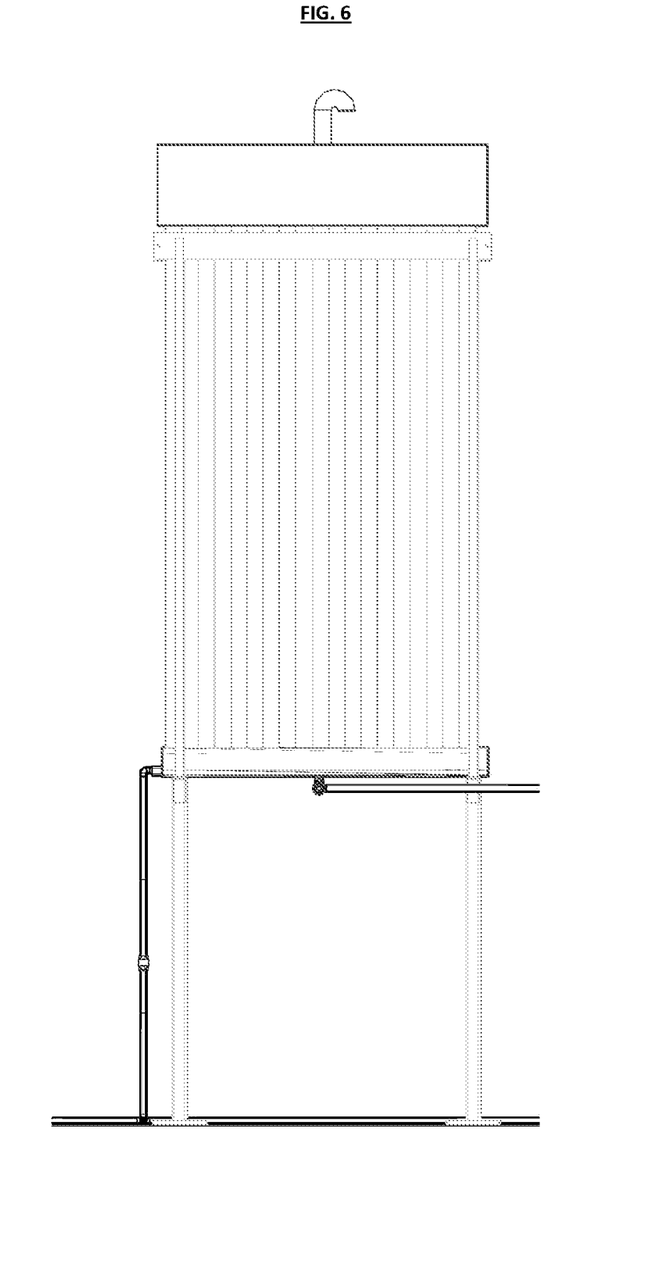
FIG. 6 is a front elevation view of the photobioreactor of this invention.
Figure 7:
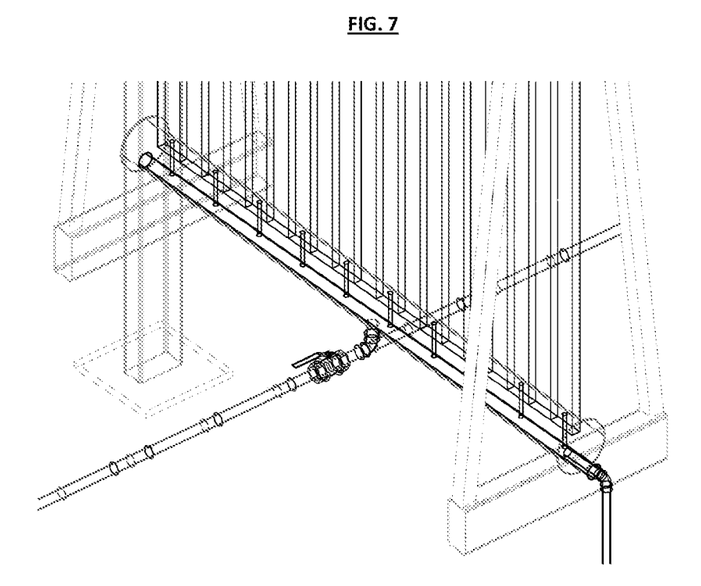
FIG. 7 is a perspective view of the distribution tube for the photobioreactor of this invention.
Figure 8:
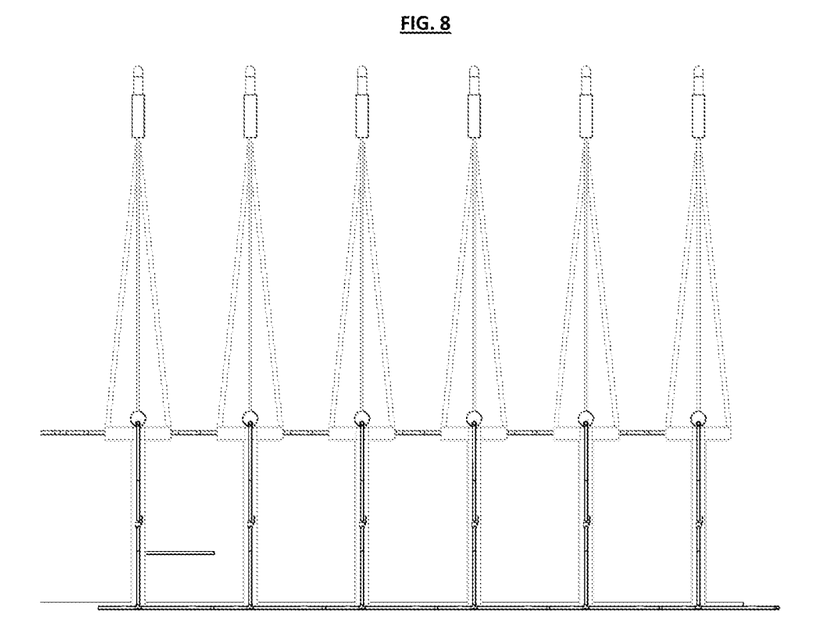
FIG. 8 is a side elevation view of a set of photobioreactors of this invention.

As is seen in FIGS. 1 through 8, the this invention's system for producing biomass from photosynthesizing microorganisms comprises:
- a gas injection assembly comprising:
- a plurality of distribution pipes (30),
- a pressurized air tank (31) connected to said gas distribution pipes (30),
- a gas inlet (32), for example $CO_2$, connected to said gas distribution pipes (30),
- a plurality of flow control valves (not shown in the figures) at the ends of said gas distribution pipes (30),
- a fresh water, brine or sea water reservoir (10) comprising:
  - a water intake (12), and
  - a water outlet (11) connected to the intake of a water pump (13),
  - said water pump (13);
- a filter (14) connected to the outlet of said water pump (13),
- a nutrient supply assembly comprising:
- a supply reservoir (20) comprising a nutrient intake (23), a water intake (22) connected to said filter (14) which receives filtered water from the water reservoir (10) and a nutrient outlet (21) connected to the intake of a nutrient pump (24),
- a nutrient source A and a nutrient source B connected to said nutrient intake (23),
- said nutrient pump (24),
- a plurality of nutrient distribution pipes (25) connected to the outlet of said nutrient pump (24),
- a first valve (26) for the first inoculation photobioreactor (41), a second valve (27) for the second inoculation photobioreactor (43), and
- a plurality of supply valves (not shown in the figures) for a plurality of culture photobioreactors (50),
- at least the first such inoculation photobioreactor (41), of the vertical, bubbling type and measuring less than 50 mm in diameter, comprising:
  - a supply intake (41*a*) connected to said first valve (26),
  - a gas injection intake (41*b*) connected to said gas distribution pipes (30) through one of the aforementioned plurality of flow control valves,
  - an inoculated culture medium collection outlet (41*c*) that discharges into a first inoculated culture medium collection tank (42), and
  - said first inoculated culture medium collection tank (42);
- at least the second such inoculation photobioreactor (43), of the vertical, bubbling type and measuring less than 100 mm in diameter, comprising:
  - a supply intake (43*a*) connected to said second valve (27),
  - a gas injection intake (43*b*) connected to said gas distribution pipes (30) through one of the aforementioned arrays of flow control valves,
  - an inoculated culture medium collection outlet (43*c*) that discharges into the second inoculated culture medium collection tank (44), and
  - said second inoculated culture medium collection tank (44);
- a plurality of cultivation photobioreactors (50) connected in parallel to said nutrient supply and to said gas injection assembly, where each comprises:
  - a transparent panel (500), made from two vertically arranged transparent sheets (505) with a separation between them with transparent parallel subdivisions (501) forming transparent cells (502), where each transparent cell (502) has one top opening (503) and one bottom opening (504), where the thickness of said transparent panel (500) is less than 2 cm,
  - a lower recirculation chamber (510) in fluid contact (536) with said bottom openings
  - (504) of the transparent cells (502);
  - wherein the fluid travels upward (534) within a given cell having a gas injector disposed proximal to its bottom due to gas rising through that given cell and fluid travels downward (535) within two cells adjacent on either side to the given cell with no gas injector disposed proximal to their respective bottoms and
  - an upper recirculation chamber (520) in fluid contact (537) with said top openings (503) of the transparent cells (502);
  - a gas distribution tube (530) externally arranged along the bottom edge of said transparent panel (500); where said gas distribution chamber (530) comprises gas injectors (531) arranged to be in fluid contact with the interior of a plurality of said transparent cells (502); and
  - a supporting structure that supports the transparent panel (500), the lower recirculation chamber (510), the upper recirculation chamber (520) and the air distribution tube (530); and
- a plurality of collection tanks (60) each connected to a photobioreactor (50), As per another aspect of the invention, it is equipped with a cultivation photobioreactor (50) for the production of biomass from photosynthesizing microorganisms, which comprises:
  a transparent panel (500) made from two vertically arranged transparent sheets (505) with a separation between them, with transparent parallel subdivisions (501) forming transparent cells (502), where each translucent cell (502) has a top opening (503) and a bottom opening (504), where the thickness of said transparent panel is less than 2 cm;

a lower recirculation chamber (510) in fluid contact with said bottom openings (504) of the transparent cells (502);

an upper recirculation chamber (520) in fluid contact with said top openings (503) of the transparent cells (502);

a gas distribution tube (530), which can be seen in FIG. 7, externally arranged along the bottom edge of said transparent panel (500); where said gas distribution tube (530) comprises gas injectors (531) arranged to be in fluid contact with the interior of a plurality of said transparent cells (502); and a supporting structure, shown in FIG. 8, that supports the transparent panel (500), the lower recirculation chamber (510), the upper recirculation chamber (520) and the air distribution tube (530).

Specifically, as per a preferred embodiment of the invention, the thickness of said transparent panel (500) is less than 1.2 cm.

As per a preferred aspect of the invention, said gas distribution tube (530) comprises gas injectors (531) alternately arranged in one out of every two adjacent transparent cells (502) to be in fluid contact with the interior of said transparent cells (502).

As per another preferred aspect of the invention, said gas distribution tube (530) comprises gas injectors (531) arranged in every transparent cell (502) and in fluid contact with the interior of said transparent cells (502).

As per one aspect of the invention, said transparent panel (500) is made out of one of the following materials: acrylic, polycarbonate or glass.

In addition, the lower recirculation chamber (510) comprises a fluid intake fitting (511) and another fluid outflow fitting (512) to allow for a plurality of photobioreactors as per this invention (50) to be connected in either a parallel or serial arrangement to form a system for obtaining biomass as per this invention.

INDUSTRIAL APPLICATION

Using the system and the photobioreactor for obtaining biomass from photosynthesizing microorganisms in this invention, it is possible to produce yields of 80 to 160 g/m$^2$ per day without artificial nighttime illumination. In addition, nighttime illumination may be provided to increase productivity yields to beyond 160 to 250 g/m$^2$ per day.

The system of this invention will allow 75% of the space available to be used: in other words, in an area of 10,000 m$^2$ (1 hectare), 7,500 m$^2$ would be used for production, while the remaining 2,500 m$^2$ are reserved for other necessary structures such as drying facilities, laboratories, pedestrian access paths, etc. This means that a 10,000 m$^2$ area without nighttime illumination can produce biomass yields between 600 and 1,200 kg/day with the system in this invention.

The biomass obtained from the system of this invention can be used to produce a variety of valuable products; for example, the oil content of the biomass can be taken to be between 20 to 30% of its weight, which can be converted into biodiesel with a yield of approximately 96.5%; therefore every 10,000 m$^2$ of land can produce between 115.8 and 173.7 kg of biodiesel per day.

The biomass produced can be estimated to have a content of 0.5% carotenoids (by mass), so that with the system of this invention, every 10,000 m$^2$ of land can yield from 3 to 6 kg of carotenoids per day.

From this same biomass produced, we can estimate a daily production of fatty acids (for example, omega 3) of around 90 to 360 kg/day for every 10,000 m$^2$ of land with the system in this invention. We can also estimate glycerol production of around 20.4 to 30.6 kg/day for every 10,000 m$^2$ of land using the system in this invention.

For biogas production, the dry material yields must be estimated: that is, the difference between the total biomass produced and the oil obtained from said biomass production; heredry material production is estimated at between 40 and 70% of the weight of the biomass obtained, which allows between 120,000 and 420,000 liters of biogas to be produced for every 10,000 m$^2$ of land using system in this invention.

The invention claimed is:

1. A system configured to facilitate production of biomass from photosynthesizing microorganisms by way of photobioreactors, the system comprising:
    a gas injection assembly comprising:
        a plurality of distribution pipes,
        a pressurized air tank connected to said gas distribution pipes, and a plurality of flow control valves at the ends of said gas distribution pipes; a fresh water, brine or sea water reservoir comprising:
        a water intake,
        a water outlet,
        a water pump with an inlet and an outlet,
        the water outlet connected to the intake of the water pump, and a filter connected to the outlet of said water pump; a nutrient supply assembly comprising:
        a supply reservoir comprising a nutrient intake,
        a supply reservoir comprising the water intake and a nutrient outlet,
        a nutrient pump with an intake and an outlet,
        a nutrient source A and a nutrient source B connected to said nutrient intake, wherein the supply reservoir water intake is connected to said filter to receive filtered water from the water reservoir,
        the nutrient outlet connected to the intake of the nutrient pump, and a plurality of nutrient distribution pipes connected to the outlet of said nutrient pump;
    at least a first inoculation photobioreactor measuring less than 50 mm in diameter, comprising:
        a first inoculation photobioreactor supply intake connected to at least one of the plurality of nutrient distribution pipes through a first valve for the first inoculation photobioreactor,
        a first inoculation photobioreactor gas injection intake connected to the gas distribution pipes through one of the plurality flow control valves,
        a first inoculated culture medium collection tank, and a first inoculated culture medium collection outlet that discharges into the first inoculated culture medium collection tank;
    at least a second inoculation photobioreactor measuring less than 100 mm in diameter, comprising:
        a second inoculation photobioreactor supply intake connected to at least one of the plurality of nutrient distribution pipes through a second valve for the second inoculation photobioreactor,
        a second inoculation photobioreactor gas injection intake connected to the gas distribution pipes through one of the plurality of flow control valves,
        a second inoculated culture medium collection tank, and a second inoculated culture medium collection outlet that discharges into the second inoculated culture medium collection tank;
    a plurality of separate cultivation photobioreactors connected parallel to each other's width, and connected to the at least one of the plurality of nutrient distribution pipes connected to the at least a first inoculation photobioreactor and the at least a second inoculation photobioreactor for the intake of the first inoculated culture medium or the second inoculated culture medium, wherein each of the plurality of separate cultivation photobioreactors is configured to be in fluid communication with a gas supply, the gas supply being in parallel connection with the plurality of cultivation photobioreactors, the gas supply being configured to provide gas to each of the plurality of separate cultivation photobioreactors, wherein each of the plurality of separate cultivation photobioreactors comprises:

a panel formed by two transparent planar sheets separated by vertical partitions that define vertical cells between the two sheets, the cells being open at the top and bottom so that the cells are in fluid communication at the top and bottom of the photobioreactor;

a plurality of gas injectors configured to introduce gas from the gas supply to the photobioreactor, individual ones of the injectors being disposed proximal to the bottom of alternating ones of the cells such that (1) fluid travels upward within a cell having a gas injector disposed proximal to its bottom due to gas rising through the cell and (2) fluid travels downward within two cells adjacent on either side of the cell, wherein the two adjacent cells have no gas injector disposed proximal to their respective bottoms and lower and upper recirculation chambers in fluid contact with said openings at the bottom and top of said vertical cells, respectively; and a plurality of collection tanks each connected to at least one of the plurality of separate cultivation photobioreactors.

2. The system of claim 1, wherein the panel has a thickness that is less than 2 centimeters.

3. The system of claim 2, wherein the panel has a thickness that is less than 1.2 centimeters.

4. The system of claim 1, wherein the two transparent planar sheets are at least 90% transparent.

5. The system of claim 1, wherein at least one of the plurality of collection tanks is in fluid communication with at least one of the plurality of separate cultivation photobioreactors, and wherein at least one of the plurality of collection tanks is configured to receive and store biomass produced in the at least one cultivation photobioreactor.

6. The system of claim 1, wherein the gas comprises carbon dioxide.

* * * * *